Figure 1:
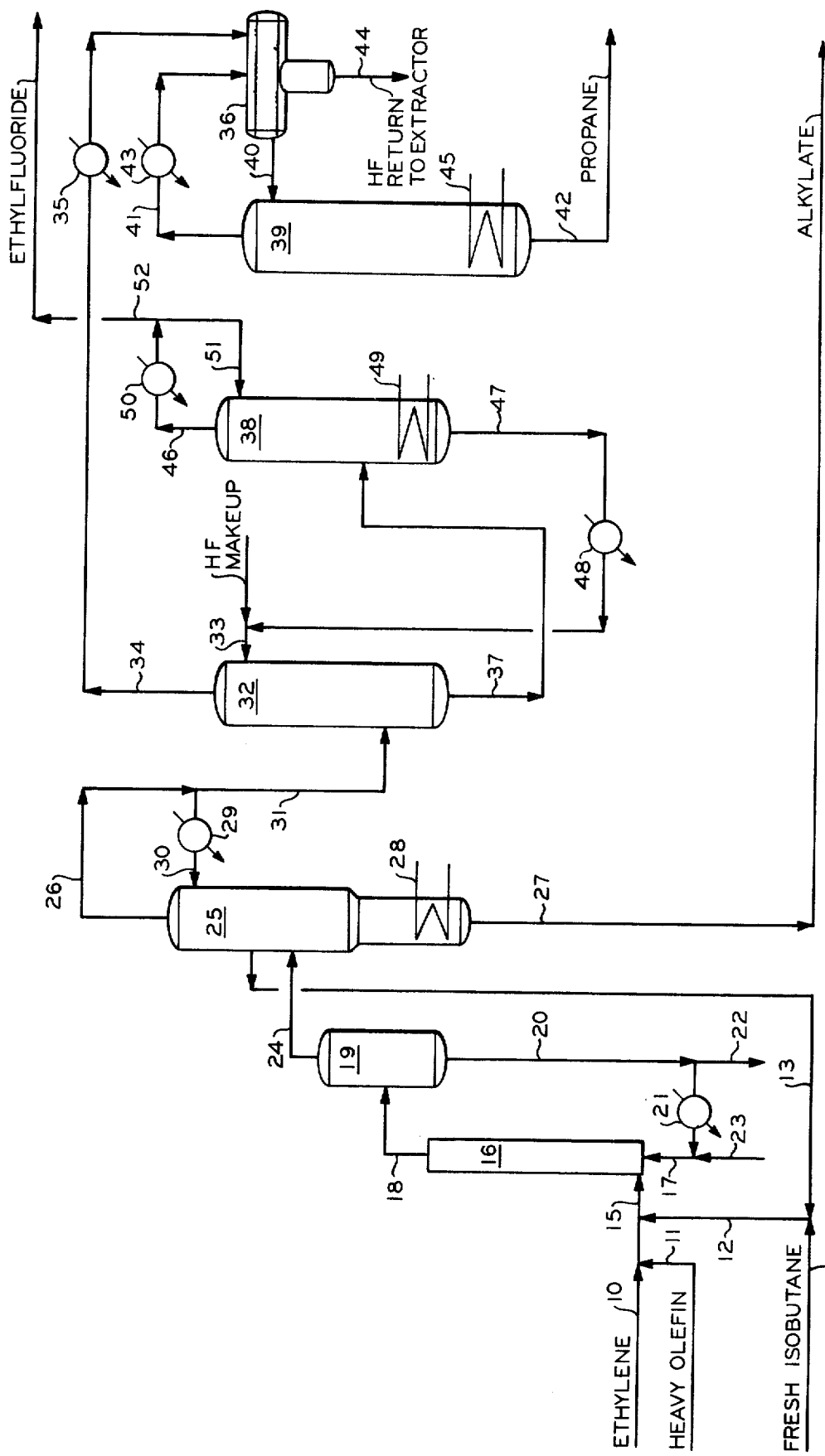

United States Patent [19]

Hutson, Jr. et al.

[11] 4,052,469

[45] Oct. 4, 1977

[54] ETHYLFLUORIDE PRODUCTION

[75] Inventors: Thomas Hutson, Jr.; Cecil O. Carter, both of Bartlesville, Okla.

[73] Assignee: Phillips Petroleum Company, Bartlesville, Okla.

[21] Appl. No.: 578,041

[22] Filed: May 16, 1975

[51] Int. Cl.² .............................................. C07C 19/08
[52] U.S. Cl. .................................................. 260/653.6
[58] Field of Search ...................................... 260/653.6

[56] References Cited

U.S. PATENT DOCUMENTS

| | | | |
|---|---|---|---|
| 2,451,843 | 10/1948 | Linn et al. | 260/653.6 |
| 2,456,435 | 12/1948 | Matuszak | 260/653.6 |
| 2,539,668 | 1/1951 | Linn et al. | 260/653.6 |
| 2,583,413 | 1/1952 | Carnell | 260/653.6 |
| 3,751,517 | 8/1973 | Hutson, Jr. et al. | 260/683.48 |
| 3,761,540 | 9/1973 | Hutson, Jr. et al. | 260/683.51 |
| 3,763,265 | 10/1973 | Hutson, Jr. et al. | 260/683.42 |

FOREIGN PATENT DOCUMENTS

| | | | |
|---|---|---|---|
| 40-17449 | 9/1965 | Japan | 260/653.6 |

*Primary Examiner*—Delbert E. Gantz
*Assistant Examiner*—J. Thierstein

[57] ABSTRACT

In the production of ethylfluoride by reacting ethylene with hydrofluoric acid, the addition of a very minor amount of a heavier olefin such as a $C_3$ and/or $C_4$ olefin greatly improves conversion and selectivity of the reaction. The product ethylfluoride can be recovered by liquid-liquid extraction.

9 Claims, 2 Drawing Figures

ETHYLFLUORIDE PRODUCTION

This invention relates to the production of ethylfluoride. In accordance with another aspect, this invention relates to an improved process for the production of ethylfluoride by reacting ethylene with hydrofluoric acid in the presence of a very minor amount of a heavier olefin which is sufficient to improve conversion and selectivity of the reaction. In accordance with another aspect, this invention relates to a process for increasing the conversion and selectivity of the reaction of ethylene with hydrofluoric acid to produce ethylfluoride by carrying out the reaction in the presence of a minor amount of propylene and/or isobutylene.

Ethylfluoride is a known chemical compound and has recently gained increased importance as a commercial item in view of its use as an additive or reactant in various chemical processes. For example, its utility as an alkylation catalyst modifier is well known, as disclosed in U.S. Pat. Nos. 3,763,265 and 3,751,517. More recently, it has been considered as a likely candidate for a feedstock in electrochemical fluorination for conversion to 1,2-difluoroethane. Thus, in view of its current importance as a commercial chemical, it is highly desirable to provide an economically feasible process for its production whereby increases yields and improved selectivity of the reaction for the production of ethylfluoride are realized. The present invention is directed to such an improved process.

Accordingly, an object of this invention is to provide an improved process for the production of ethylfluoride.

Another object of this invention is to provide a process whereby improved conversion and selectivity in the production of ethylfluoride are realized.

Another object of this invention is to provide an economically feasible process for the production of ethylfluoride.

Other objects and aspects, as well as the several advantages of the invention will be apparent to those skilled in the art upon reading the specification, the drawing, and the appended claims.

In accordance with the invention, an improved process for the production of ethylfluoride is provided which comprises reacting ethylene with hydrofluoric acid in the presence of a minor amount of a heavier olefin sufficient to increase the conversion and selectivity of the reaction.

In accordance with one embodiment of the invention, ethylene is reacted with hydrofluoric acid in the presence of propylene and/or isobutylene to increase conversion and improve selectivity of the reaction.

In accordance with another embodiment, the reaction of ethylene with hydrofluoric acid and a minor amount of a heavier olefin is carried out in the presence of a paraffinic hydrocarbon diluent.

In accordance with one specific embodiment, ethylene is reacted with hydrofluoric acid in the presence of propylene and/or isobutylene to increase conversion and improve selectivity of the reaction, and the product phase comprising ethylfluoride, propane, and HF recovered from the reaction effluent is subjected to extraction by contacting with liquid hydrofluoric acid under conditions to remove ethylfluoride from the product phase and stripping ethylfluoride from HF to recover same as product.

It has been found that ethylene can be very efficiently converted to ethylfluoride by reaction with hydrogen fluoride in the presence of a heavier olefin wherein the concentration of heavier olefin in the feed is kept low, less than 30 percent of the total olefin and preferably less than 10 percent of the total olefin. Accordingly, the concentration of heavier olefin can range from 0.01 to 30 weight percent of the total olefin, preferably 0.01 to 10 weight percent of the total olefin, which is sufficient to increase the conversion and improve selectivity of the reaction.

The heavier olefins that can be used as reaction promoters according to the invention are the $C_3$ and $C_4$ olefins represented by propylene, isobutylene, butene-1, and butene-2. Mixtures of these heavier olefins can be used if desired. Propylene and isobutylene are presently preferred heavy olefin promoters.

The reaction of ethylene with hydrogen fluoride and the heavier olefin reaction promoter can be carried out in the presence of a reaction diluent which is inert to the reaction. Presently preferred reaction diluents include the lower paraffins such as propane, n-butane, and other light hydrocarbons.

The reaction of ethylene with hydrogen fluoride is carried out under reaction conditions conducive to the production of ethylfluoride and in the presence of a sufficient minor amount of a higher olefin, as defined, to increase conversion and improve selectivity of the reaction. The reaction temperature can vary appreciably, but will generally be in the range 50°–160° F (10°–71° C), preferably 100°–160° F (38°–71° C), as the generally higher temperatures favor ethylene conversion and selectivity. The reactor residence time will ordinarily range from about 10 to about 240 seconds. The molal ratio of reaction diluent to olefin will range from 8 to 30. It has been found that higher diluent to olefin ratios favor selectivity to ethylfluoride.

In actual operation, ethylene and hydrogen fluoride are contacted in the presence of a higher $C_3$ and/or $C_4$ olefin in a suitable reaction zone under conditions to produce ethylfluoride. The effluent from the reaction zone is allowed to separate into an HF acid phase and a product phase comprising ethylfluoride and unreacted ethylene and/or higher olefin. The product phase can be subjected to liquid-liquid extraction to recover ethylfluoride, reaction diluent, HF, and other materials in the reactor effluent.

Given the foregoing description, one skilled in the art having studied the same can determine by mere routing testing the design and conditions of operation required to carry out the invention. However, to more fully describe the invention and to set forth a now best mode contemplated for it in its application in the formation of ethylfluoride by the reaction of ethylene with hydrogen fluoride in the presence of isobutylene as the higher olefin promoter and isobutane as the reaction diluent, reference is had to FIG. 1.

Figure 2:
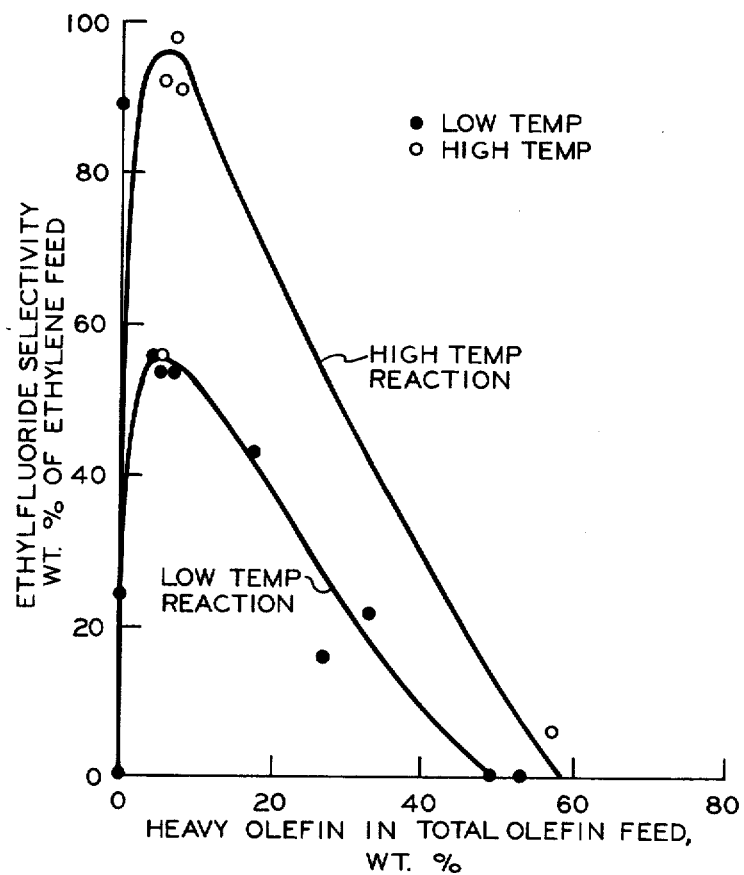

FIG. 1 is a flow chart showing the production of ethylfluoride by reacting ethylene with hydrogen fluoride in the presence of small amounts of heavy olefin. FIG. 2 is a graph which plots the ethylfluoride selectivity by weight percent of ethylene feed against the presence of heavy olefin in the total olefin feed also expressed in weight precent.

Referring now to FIG. 1, ethylene in line 10 is mixed with isobutylene, the heavier olefin reaction promoter introduced in line 11, together with isobutane reaction diluent introduced by line 12. Isobutane in line 12 can include recycle isobutane introduced by line 13, as well as make-up fresh isobutane introduced by way of line 14. The feed mixture of ethylene, isobutylene, and isobutane reaction diluent is passed by way of line 15 and introduced into in-line reactor 16 wherein the feed mixture is contacted with hydrogen fluoride introduced by way of line 17.

In reactor 16, feedstock and hydrogen fluoride are subjected to reaction conditions conducive to the reaction of ethylene with hydrogen fluoride to produce ethylfluoride. The reaction effluent from reactor 16 is passed by way of line 18 to settler 19 wherein the reaction effluent is allowed to separate into a lower HF acid phase and an upper product phase comprising ethylfluoride, isobutane, butane, propane, and a minor amount of alkylate.

The lower HF acid phase is removed from the bottom of settler 19 by way of line 20 and passed through cooler 21 before being mixed with feed in line 15 by way of line 17. If desired, a portion of the HF acid phase removed from settler 19 can be passed to an HF rerun unit (not shown) for reprocessing by way of line 22. Rerun HF acid and make-up acid can be introduced by way of line 23.

The upper product phase in settler 19 is removed therefrom by way of line 24 and passed to isostripper zone 25 wherein the product phase is subjected to conditions of temperature and pressure sufficient to take overhead a stream comprising ethylfluoride, propane, and HF by way of line 26, and a bottom stream comprising alkylate by way of line 27. Typical conditions for column 25 include a pressure of 125 psig, a top temperature of 80° F (27° C), and a kettle temperature of 350° F (177° C). A source of heat for column 25 is introduced thereto by way of coil 28.

A portion of the overhead stream comprising ethylfluoride, propane, and HF is passed through condenser 29, and the condensate is returned to column 25 as reflux by way of line 30. The remainder of the overhead in line 26 is passed by way of line 31 to ethylfluoride extractor zone 32. In zone 32 the feed stream comprising ethylfluoride, propane, and HF is passed upwardly countercurrent to lean HF absorbent introduced by line 33 under conditions sufficient to take overhead by way of line 34 a stream comprising propane and HF which is cooled by condenser 35 and then passed to accumulator 36. A bottoms stream 37 comprising HF and ethylfluoride is removed from extractor 32 and passed to ethylfluoride column 38. Typical conditions in ethylfluoride extractor 32 include a pressure of 110 psig and a temperature of 90° F (32° C).

A portion of the condensate in accumulator 36 comprising HF acid and propane is passed to HF stripper 39 by way of line 40 and subjected to conditions sufficient to strip HF overhead by line 41 and remove propane as bottoms by line 42. HF stripper 39 is typically operated under conditions including a pressure of 250 psig, a top temperature of 100° F (38° C), and a kettle temperature of 130° F (54° C), such that HF is taken overhead by way of line 41 and bottoms comprising propane by way of line 42. Heat can be supplied to column 39 by coil 45. The overhead stream 41 is passed through condenser 43 and introduced into overhead accumulator 36. HF acid is withdrawn from accumulator 36 by way of line 44 and can be returned to settler 19 if desired.

The bottoms stream 37 comprising HF absorbent enriched with ethylfluoride is subjected to conditions in column 38 sufficient to take overhead a stream 46 comprising ethylfluoride and a bottoms stream 47 comprising lean HF absorbent which is returned to extractor 32 after being cooled in exchanger 48. Heat is supplied to column 38 by coil 49. Typical conditions in column 38 include a pressure of 50 psig, a top temperature of 32° F (0° C), and a kettle temperature of 150° F (66° C).

The overhead stream 46 comprising ethylfluoride is cooled in condenser 50. A portion of the cooled overhead stream is returned to column 38 as reflux by line 51, and the remainder of the cooled stream is recovered as product by line 52.

SPECIFIC EXAMPLE

A series of pilot plant runs were carried out for the production of ethylfluoride by reacting ethylene with hydrogen fluoride in accordance with the invention in the presence of a higher olefin promoter. Specifically, a series of runs were carried out using isobutylene as the higher olefin promoter and another series of runs carried out using propylene as the higher olefin promoter.

The reaction conditions, reactants, and other process information are included in data presented in Table I.

TABLE I

| Promoter | Isobutylene | | | | None | | | Propylene | | |
|---|---|---|---|---|---|---|---|---|---|---|
| Run Number | 984 | 985 | 1164 | 1165 | 1083 | 1087 | C | 1185 | 1188 | 1189 |
| Reactor Temperature, ° C | 21 | 54 | 64 | 32 | 38 | 38 | 24 | 64 | 35 | 65 |
| Reactor Temperature, ° F | 70 | 129 | 147 | 90 | 100 | 100 | 75 | 147 | 95 | 149 |
| Pressure, psig | 190 | 190 | 190 | 190 | 190 | 190 | 190 | 190 | 190 | 190 |
| Molal Ratio, $C_4$/Olefin | 8.4 | 8.4 | 18.9 | 19.7 | 7.4 | 1.8 | 6.9 | 18.6 | 13.9 | 14.8 |
| Heavy Olefin, Wt. % of Total Olefin | 5.2 | 5.2 | 7.3 | 7.2 | — | — | — | 7.6 | 5.5 | 5.9 |
| Ethylene Conversion, % | 87.4 | 97.6 | 98.3 | 91.4 | 71.9 | 77.8 | Trace | 96.8 | 87.1 | 96.6 |
| Selectivity to $C_2H_5F$, % | 56.3 | 56.3 | 98.1 | 53.9 | 89.4 | 23.7 | Trace | 90.8 | 54.0 | 91.7 |
| Alkylate Yield, lb/lb Olefin | 0.4 | 0.9 | 0.7 | 0.4 | 0.7 | 0.3 | 0 | 0.4 | 0.6 | 0.4 |
| Calculated Residence Time, sec. | 34 | 183 | 79 | 46 | 19(?) | 102 | 103 | 43 | 76 | 60 |

In all of the runs set forth in Table I, isobutane was used as diluent. It will be noted from the data in Table I that, in general, higher temperatures favor ethylene conversion and selectivity. It should also be noted from the data in Table I that higher isobutane to olefin ratios favor selectivity to ethylfluoride.

All of the data in Table I are plotted in FIG. 2 to illustrate the effect of temperature on ethylfluoride selectivity as a function of heavy olefin concentration in the olefin feed. Also included in the plot in FIG. 2 are the data from Runs A, B, C, E, L, M, and O which appear in Examples II and III of U.S. Pat. No. 3,761,540 by the same invention.

There are considerable scatter in the data, as might be expected from pilot plant runs which were not specifically set up to support the invention, but the biggest "problem" run is number 1083 which had no heavy olefin in the feed, was run at a relatively low temperature of 100° F (38° C), and gave rather high conversion and selectivity of ethylene to EF. On examination of the plant log, it was discovered that the run preceding run 1083 had been an alkylation run using high isobutylene concentrations. It appears most probable that the reactor system was not adequately cleaned out after the run, and the system contained some unknown level of isobutane. This theory is also supported by the relatively high alkylate yield, 0.7 lb/lb olefin. Run C in Table I is taken from U.S. Pat. No. 3,761,540 and shows no ethylene conversion in the absence of heavy olefin at 75° F reactor temperature. Run 1087 also had no heavy olefin feed but attained 77.8% ethylene conversion and 23.7% selectivity to EF. The higher reactor temperature of 100° F is believed to explain the difference between this run and Run C.

We claim:

1. A process for the production of ethylfluoride which comprises reacting ethylene with hydrogen fluoride under conditions which produce ethylfluoride as the major or primary product and in the presence of at least one heavier $C_3$ and $C_4$ olefin in a minor amount ranging from 0.01 to 30 weight percent of the total olefin present which is sufficient to increase the conversion and improve the selectivity of the reaction.

2. A process according to claim 1 wherein the amount of heavier olefin present during said reacting ranges from 0.01 to 10 weight percent of the total olefin present.

3. A process according to claim 1 wherein the amount of heavier olefin present does not exceed about 10 weight percent of the total olefin present and further wherein the reaction is carried out in a lower paraffinic hydrocarbon reaction diluent.

4. A process according to claim 1 wherein said reacting is carried out at a temperature in the range of 50°-160° F (10°-71° C) for a period of time ranging from about 10 to about 240 seconds in the presence of a lower paraffinic hydrocarbon diluent wherein the ratio of paraffin to olefin in the reaction ranges from 8-30 on a molal ratio.

5. A process according to claim 1 wherein said higher olefin is isobutylene or propylene, the amount of isobutylene or propylene present during said reacting does not exceed 10 weight percent of the total olefin present, and the reacting is carried out in an isobutane reaction diluent.

6. A process according to claim 5 wherein said reacting is carried out at a temperature in the range of 100°-160° F (38°-71° C) and a weight ratio of olefin to hydrogen fluoride in the range of 5-1.

7. A process according to claim 1 further comprising the steps of
   a. passing the effluent from said reacting to a phase separation zone to recover a product phase comprising ethyl-fluoride, HF, propane, and other materials and
   b. separating said product phase into an ethylfluoride fraction, a propane fraction, and an HF fraction.

8. A process according to claim 1 further comprising the steps of
   a. passing the effluent from said reacting to a phase separation zone to recover a product phase comprising ethylfluoride, HF, propane, and other materials,
   b. subjecting said product phase to liquid-liquid extraction by contacting with lean HF under conditions to absorb ethylfluoride and recover an overhead from said extraction comprising propane and HF,
   c. stripping ethylfluoride absorbed in HF under conditions sufficient to remove ethylfluoride overhead as product and returning lean HF to step (b), and
   d. heating said overhead recovered in step (b) to remove HF therefrom, leaving propane as product.

9. A process according to claim 1 wherein the amount of heavier olefin present during said reacting ranges from 0.01 to 10 weight percent of the total olefin present, said reacting is carried out at a temperature in the range of 50°-160° F (10°-71° C) for a period of time ranging from about 10 to about 240 seconds.

* * * * *